United States Patent [19]

Lipp et al.

[11] Patent Number: 5,904,931
[45] Date of Patent: May 18, 1999

[54] TRANSDERMAL THERAPEUTIC SYSTEMS THAT CONTAIN SEX STEROIDS AND DIMETHYL ISOSORBIDE

[75] Inventors: Ralph Lipp; Clemens Gunther; Jutta Riedl; Ulrich Tauber, all of Berlin, Germany

[73] Assignee: Schering Aktiengesellschaft, Berlin, Germany

[21] Appl. No.: 08/693,050

[22] PCT Filed: Feb. 9, 1995

[86] PCT No.: PCT/EP95/00483

§ 371 Date: Nov. 8, 1996

§ 102(e) Date: Nov. 8, 1996

[87] PCT Pub. No.: WO95/22322

PCT Pub. Date: Aug. 24, 1995

[30] Foreign Application Priority Data

Feb. 18, 1994 [DE] Germany ............... 44 05 898

[51] Int. Cl.⁶ ............................................. A61F 13/00
[52] U.S. Cl. .................. 424/449; 424/447; 424/448
[58] Field of Search ............................ 424/447, 448, 424/449

[56] References Cited

U.S. PATENT DOCUMENTS

| | | | |
|---|---|---|---|
| 4,082,881 | 4/1978 | Chen et al. | 514/39 |
| 5,071,657 | 12/1991 | Oloff et al. | 424/486 |
| 5,393,529 | 2/1995 | Hoffmann et al. | 424/445 |
| 5,538,736 | 7/1996 | Hoffmann et al. | 424/448 |

FOREIGN PATENT DOCUMENTS

89/04179  5/1989  WIPO.

*Primary Examiner*—D. Gabrielle Brouillette
*Attorney, Agent, or Firm*—Millen, White, Zelano & Branigan, P.C.

[57] ABSTRACT

Transdermal therapeutic systems that contain sex steroids and optionally penetration-enhancers and crystallization inhibitors are described, which are characterized in that they contain dimethyl isosorbide, with the exception of systems that contain active ingredient-containing, non-free-flowing gel phases or 3-keto-desogestrel.

20 Claims, 1 Drawing Sheet

TRANSDERMAL THERAPEUTIC SYSTEMS THAT CONTAIN SEX STEROIDS AND DIMETHYL ISOSORBIDE

This application is a 371 of PCT/EP95/00483, filed Feb. 9, 1995.

The invention relates to transdermal therapeutic systems that contain sex steroids and optionally penetration-enhancers and crystallization inhibitors, which are characterized in that they contain dimethyl isosorbide, with the exception of systems that contain active ingredient-containing, non-free-flowing gel phases or 3-ketodesogestrel.

According to the invention, sex steroids are to be defined preferably as gestagens and/or estrogens although, in principle, other sex steroids, such as androgens, antiestrogens or antigestagens, are suitable for the production of the agent according to the invention.

Suitable gestagens for the agent according to the invention are, for example, gestodene, levonorgestrel, desogestrel, norethisterone and norethisterone acetate. For the production of the agent according to the invention, 3-ketodesogestrel is also suitable, as indicated by PCT/EP93/02224, which had not yet been prepublished as of the time of priority of this application.

Estrogens that are suitable for the agent according to the invention are, for example, estradiol, estriol, ethinylestradiol, mestranol, 14α,17α-ethanoestra-1,3,5(10)-triene-3,17β-diol (WO 88/01275), 14α,17α-ethanoestra-1,3,5(10)-triene-3β,16α,17α-ethanoestra-1,3,5(10)-triene-3β,16α,17α-triol (WO91/08219) and their esters (EP-A 163596), such as estradiol-dipropionate, estradiol-dihexanoate and estradiol-didecanoate. In addition to at least one gestagen, the combination preparations according to the invention preferably contain 1 to 3—especially 1 to 2—estrogen(s).

EP-B 0 137 278, which relates to transdermal therapeutic systems in which the active ingredient is embedded in a non-free-flowing gel phase, contains a general reference stating that dimethyl isosorbide can also be used in them as a solvent, but the patent specification does not indicate that the use of this agent could be of special benefit in the case of transdermal therapeutic systems.

As is generally known, therapeutic systems that are to be administered transdermally have the advantage that they make possible a more uniform release of the active ingredient over a longer period than is generally possible with other agents that are to be administered in other ways—such as, for example, perorally. These properties can be used advantageously in the case of a number of endocrine diseases. For sparingly water-soluble steroid hormones, such as, for example, gestagens, however, it is generally quite problematical to provide transdermal systems that ensure a level of penetration of the active ingredient through the skin that is sufficient for treatment.

With the aid of the agent according to the invention, which in addition to sex steroid(s) also contains dimethyl isosorbide, it has now been found that it is possible, surprisingly enough, to achieve a therapeutically adequate, very uniform rate of penetration of the steroid hormones through the skin, while this is only conditionally possible with the known steroid hormones that contain agents that are to be administered transdermally (EP-A 137278 and EP-A 275716), which makes it necessary to use comparatively large systems.

Dimethyl isosorbide is a substance of formula

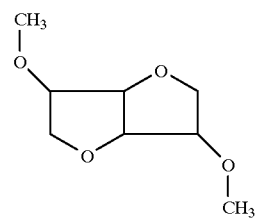

As is generally known, it is a substance with good dissolving power for organic compounds (H. P. Fiedler, Lexikon der Hilfsstoffe für Pharmazie, Kosmetik und angrenzende Gebiete [Dictionary of Adjuvants for Pharmaceutics, Cosmetics and Related Fields], Editio Cantor Aulendorf, 1989). This is used in, for example, U.S. Pat. No. 4,082,881 to keep high concentrations of organic pharmaceutical substances dissolved in various topical preparations, but not in transdermal systems. In U.S. Pat. No. 4,814,173, dimethyl isosorbide is used as a solvent for various pharmaceutical substances, but not for sex steroids, in solutions, emulsions as well as in complex synthesized transdermal therapeutic systems based on silicone skin contact adhesives.

It has now been found that dimethyl isosorbide is able to dissolve a number of sex steroids to a considerable extent. A selection of these steroids is presented in Tab. 1. Especially levonorgestrel, which is only slightly soluble in most standard vehicles for transdermal use, can be dissolved in dimethyl isosorbide at significantly higher concentrations.

TABLE 1

Solubility of Sex Steroids in Vehicles for Transdermal Use

| Sex Steroid | Vehicle | | | | |
|---|---|---|---|---|---|
| | Dimethyl isosorbide | Paraffin | Isopropyl myristate | Tween 80 | 1,2-Propanediol |
| Levonorgestrel | 9.0 | 0.006 | 0.42 | 3.2 | 1.0 |
| Gestodene | 74 | 0.022 | 2.2 | 18.7 | 13.4 |
| Estradiol | 55 | 0.008 | 1.5 | 34 | 84.4 |

Data in mg per ml

Moreover, dimethyl isosorbide evens out the solubilities of gestagens and estrogens. This is a significant added advantage, especially for the development of combination transdermal systems, since consequently, for the first time, highly concentrated binary mixtures of gestagens and estrogens can be dispersed together in a matrix in a molecularly disperse manner at advantageous concentration ratios of about 5:1 to 1:5. This ensures that both active ingredients are present simultaneously in high thermodynamic activity in the system.

As described in DD-A-217989, dimethyl isosorbide can be mixed to a suitable extent with skin contact adhesives that are commonly used for the production of transdermal systems.

It has now been found that certain mixed systems that consist of skin contact adhesives and dimethyl isosorbide exhibit significantly elevated dissolving power for sex steroids compared to systems without dimethyl isosorbide. These new systems, whose structure is depicted in FIG. 1, are single-phase, in contrast to the sex steroid-containing siloprene systems mentioned in EP-A 0 137 278, and are distinguished in that they adhere independently to the skin.

Also, they differ from the topical preparations mentioned in WO 89/04179, especially the active ingredient-containing plasters mentioned there, because of their simple structure. They can be produced more simply than the above-named transdermal systems and are distinguished by more advantageous wearing properties owing to their thin, flexible design.

In addition to its good properties for dissolving organic molecules, dimethyl isosorbide also has penetration-enhancing properties. Thus, surprisingly enough, in-vitro penetration studies have revealed that the vehicle dimethyl isosorbide has strong penetration-promoting properties for sex steroids (see Tab. 2).

In the agents according to the invention, normally 1 to 40% by weight and preferably 5 to 25% by weight of dimethyl isosorbide, relative to the entire active ingredient phase, is used.

TABLE 2

Percutaneous Resorption (in $\mu g/cm^2/h$) of Sex Steroids in Formulations Without Penetration Enhancers through the Skin of Hairless Mice

| Steroid | Formulation | Average Flow Day 1 | Average Flow Day 2 | Maximum Flow |
|---|---|---|---|---|
| 0.2 mg of LN | PG | 0.18 ± 0.06 | 0.53 ± 0.07 | 0.74 ± 0.14 |
| 0.2 mg of LN | PGML | 0.25 ± 0.06 | 0.42 ± 0.03 | 0.64 ± 0.06 |
| 0.2 mg of LN | DMI | 0.31 ± 0.14 | 0.66 ± 0.10 | 1.23 ± 0.32 |
| 1 mg of LN | DMI | 0.62 ± 0.20 | 1.02 ± 0.40 | 1.62 ± 0.61 |
| 0.2 mg of LN | IPM | 0.13 | 0.11 | 0.16 |
| 0.2 mg of $E_2$ | DMI | 0.51 ± 0.17 | 0.79 ± 0.48 | 0.97 ± 0.57 |
| 1 mg of $E_2$ | DMI | 2.63 ± 1.21 | 3.10 ± 1.99 | 4.17 ± 1.57 |
| 0.2 mg of $E_2$ | PG | 0.92 ± 0.26 | 0.25 ± 0.01 | 1.34 ± 0.24 |
| 0.2 mg of $E_2$ | IPM | 0.47 | 0.29 | 0.69 |

DMI: Dimethyl isosorbide
IPM: isopropyl myristate
PG: propylene glycol
PGML: propylene glycol monolaurate
LN: levonorgestrel
E2: estradiol The transdermal flows of sex steroids that are achieved in vitro can be even further increased by properly combining dimethyl isosorbide with other known penetration enhancers (see Tab. 3).

TABLE 3

Percutaneous Resorption (in $\mu g/cm^2/h$) of Sex Steroids in Formulations with Penetration Enhancers through the Skin of Hairless Mice

| Steroid | Formulation | Average Flow Day 1 | Average Flow Day 2 | Maximum Flow |
|---|---|---|---|---|
| 0.2 mg of LN | DMI + 10% LA | 1.70 ± 0.18 | 0.91 ± 0.16 | 3.62 ± 0.76 |
| 0.2 mg of LN | DMI + 10% LS | 1.95 ± 0.81 | 1.27 ± 0.62 | 3.28 ± 1.40 |
| 0.2 mg of LN | PG + 10% LA | 0.67 ± 0.04 | 0.64 ± 0.11 | 1.32 ± 0.05 |
| 0.2 mg of LN | PG + 5% azone | 0.71 ± 0.22 | 0.75 ± 0.16 | 1.13 ± 0.43 |
| 0.2 mg of $E_2$ | DMI + 10% LA | 7.35 ± 1.15 | 4.86 ± 1.97 | 11.57 ± 1.72 |
| 0.2 mg of $E_2$ | DMI + 10% LS | 9.06 ± 0.50 | 7.55 ± 0.33 | 15.29 ± 0.61 |
| 0.2 mg of $E_2$ | PG + 5% azone | 1.92 ± 0.18 | 0.90 ± 0.10 | 5.15 ± 0.84 |

With the aid of the agent according to the invention, transdermal therapeutic systems can be produced with high concentrations of sex steroids that are dissolved in a molecular disperse way. When using these new systems, an especially high effective concentration gradient between pharmaceutical agent and skin is achieved. The high concentration gradient and the strong penetration-promoting action of the dimethyl isosorbide or the dimethyl isosorbide-enhancer combinations, respectively, together produce the high transdermal flows of the processed steroid hormones.

In individual cases, an addition of crystallization inhibitors to the matrix of the previously mentioned systems, as described in WO 93/08795, can improve the shelf life of the transdermal systems according to the invention.

Very uniform administration with a set dosage of the active ingredient or active ingredient mixture can be achieved if the active ingredient or the mixture is embedded in a transdermal therapeutic system (TTS) and here especially in a matrix system. Suitable matrix systems are those that are usually used for percutaneous administration of active ingredients (Yie W. Chien: "Transdermal Controlled Systemic Medications," Marcel Dekker, Inc., New York and Basel, 1987, Dr. Richard Baker: "Analysis of Transdermal Drug Delivery Patents 1934 to 1984" and "Analysis of Recent Transdermal Delivery Patents, 1984–1986 and Enhancers" Membrane Technology & Research 1030 Hamilton Court Menlo Park, Calif. 94025 (415) 328-2228).

Thus, for example, a transdermal therapeutic system can be used, which consists of a) an impermeable cover layer,
one to three matrix layer(s) that adhere to the cover layer and that contain gestagen and/or estrogen, and dimethyl isosorbide and optionally penetration-enhancing agents and one or more crystallization inhibitors that are permeable and self-adhesive to these components or are covered or surrounded by a skin contact adhesive that optionally contains penetration-enhancing agents; a removable protective layer, or b) a cover that is provided with a contact adhesive that optionally contains penetration-enhancing agents,
one to three matrix layer(s) that leave uncovered a contact adhesive border and that are attached by means of a cover to the contact adhesive, gestagen and/or estrogen and dimethyl isosorbide and that optionally contain penetration-enhancing agents and crystallization inhibitors; and a removable protective layer.

A transdermal therapeutic system according to variant a) represents a simple matrix system. It can be, for example, of round, oval or rectangular shape and can be produced as follows.

A solution of up to 25% by weight of active ingredient or active ingredient mixture, 1–40% by weight of dimethyl isosorbide or a mixture of dimethyl isosorbide and other penetration-enhancing agents, 30–70% by weight of a medicinally usual adhesive filled up with a suitable volatile solvent to 100% by weight is coated with a plane, impermeable cover layer. After drying, a second and optionally later even a third layer, that optionally contains active ingredients, penetration-enhancing agents and adhesives, can be applied on this layer and dried. Then, the matrix system is provided with a removable protective layer.

If a medicinally usual matrix former is used, which does not adhere or insufficiently adheres to the skin after the system is dried, the system can be covered or surrounded in addition with a skin contact adhesive before the removable protective layer is applied.

Suitable volatile solvents are, for example, lower alcohols, ketones or lower carboxylic acid esters, such as ethanol, isopropanol, acetone or ethyl acetate, polar ethers, such as tetrahydrofuran, lower hydrocarbons, such as cyclohexane or benzine, or else halogenated hydrocarbons, such as dichloromethane, trichloromethane, trichlorotrifluoroethane and trichlorofluoromethane. There is no need for an explanation that mixtures of these solvents are also suitable.

Suitable penetration-enhancing agents are, for example, monovalent or multivalent alcohols, such as ethanol, 1,2-propanediol or benzyl alcohol, saturated and unsaturated fatty alcohols with 8 to 18 carbon atoms, such as lauryl alcohol or cetyl alcohol, hydrocarbons, such as mineral oil, saturated and unsaturated fatty acids with 8 to 18 carbon atoms, such as stearic acid or oleic acid, fatty acid esters with up to 24 carbon atoms or dicarboxylic acid diesters with up to 24 carbon atoms.

As medicinally usual adhesives, for example, polyacrylates, silicones, polyurethanes, block polymers, styrene-butadiene copolymers as well as natural or synthetic rubbers, such as, e.g., polyisobutylenes and especially polyacrylates, are suitable. As additional matrix formers, cellulose ether, polyvinyl compounds or silicates are to be considered. To increase the stickiness, the usual additives, such as, for example, tackifying resins and oils, can be added to the matrix obtained.

Fatty acid esters, which are suitable for the agent according to the invention, are, for example, those of acetic acid, caproic acid, lauric acid, myristic acid, stearic acid and palmitic acid, such as, for example, methyl ester, ethyl ester, propyl ester, isopropyl ester, butyl ester, sec-butyl ester, isobutyl ester, tert-butyl ester or monoglyceric acid esters of these acids. Especially preferred esters are those of myristic acid or oleic acid, such as their methyl esters and especially their isopropyl esters. Suitable dicarboxylic acid diesters are, for example, diisopropyl adipate, diisobutyl adipate and diisopropyl sebacate.

Other penetration-enhancing agents are phosphatide derivatives, such as lecithin, terpenes, amides, ketones, urea and its derivatives or ethers, such as, for example, dimethyl isosorbide and diethylene glycol monoethyl ether. There is no need for a more detailed explanation that also mixtures of these penetration-enhancing agents are suitable for the production of the agent according to the invention.

As crystallization inhibitors, which in individual cases can improve the storage stability of the systems according to the invention, for example, additives of highly dispersed silicon dioxide or macromolecular substances, such as polyvinylpyrrolidone (for example, Kollidon 12 PF, Kollidon 17 PF, Kollidon 25 and Kollidon 30 of BASF), vinylpyrrolidone-vinyl acetate copolymer (for example, Kollidon VA 64 of BASF), crosslinked polyvinylpyrrolidone, polyvinyl alcohol, hydroxypropyl cellulose, ethyl cellulose, gelatin, starch (derivatives) and dextran are suitable.

As protective layers, all films that are usually used in transdermal therapeutic systems are suitable. Such films are, for example, siliconized or fluoropolymer-coated.

As a cover layer, for example, 10 to 100 $\mu$m-thick films made of polyethylene or polyester can be used selectively pigmented or metallized in this system. The pharmaceutical agent layer applied on it preferably has a thickness of 20 to 500 $\mu$m. The release of the active ingredients usually takes place over a surface area of 1–100 cm$^2$ and preferably less than 5 to 100 cm$^2$.

In the case of multilayer matrix systems, gestagen, dimethyl isosorbide and optionally penetration-enhancers can be introduced, for example, in the matrix applied on the impermeable cover layer, while the layer or layers below contain the estrogens in addition to dimethyl isosorbide and optionally also penetration-enhancers. In contrast, however, it is also possible in such a transdermal system to arrange several active ingredient-containing matrix systems side by side.

A transdermal therapeutic matrix system according to variant b can be, for example, also round, oval or rectangular and can be produced as follows:

A cover is coated with a skin contact adhesive. Then, one or two punched-out areas of a matrix layer that is provided with an impermeable cover and that contains gestagen, dimethyl isosorbide, optionally estrogen(s) and optionally penetration-enhancing agents, is bonded to the cover pro TTS, so that the cover has a sufficient edge for attaching to the skin and also sufficient interspaces in several areas and provides it with a removable protective layer. The materials that are used in this matrix system can be the same as in those of variant a.

In addition to dimethyl isosorbide, the above-mentioned penetration-enhancing agents can be used in this system. As a permeable polymer layer, for example, a 20 to 200 $\mu$m-thick film made of cellulose esters, cellulose ethers, silicones or polyolefin compounds is used. By variation of this polymer layer, the rate of diffusion of the active ingredient or active ingredient mixture can vary within wide limits.

As an adhesive and protective layer, the same materials that are described in the transdermal therapeutic system according to variant a are suitable.

In the production of transdermal therapeutic systems with two active ingredient-containing matrix layers or pharmaceutical agent reservoirs that are arranged side by side, it is often suitable to introduce gestagen in one and estrogen in the other. In such cases, the active ingredient-containing matrix systems or pharmaceutical agent reservoirs can contain not only different active ingredients, but in addition different penetration-enhancing agents.

In the case of the matrix systems according to variant a or b, care must be taken for a sufficient spacing of the areas to prevent a diffusion of the active ingredients in the respective other area.

BRIEF DESCRIPTION OF THE DRAWINGS

Other features of the transdermal systems according to the invention can be explained based on the attached drawings that are not true-to-scale.

The gestagen agents for transdermal administration according to the invention can be used for treating the same diseases as the previously known agents, for example, agents to be administered orally, that contain highly effective gestagens. Moreover, the optionally estrogen-containing preparations according to the invention also can be used for contraception and for substitution therapy in post-menopause. The agents according to the invention have special advantages in the treatment of diseases that require a long-term treatment at relatively high dosage of the active ingredients. Here, the frequency of administration can be significantly reduced and an essentially uniform blood plasma level can be achieved. Further, it is advantageous that no gastrointestinal side effects are to be expected, and in estrogen-containing combination preparations, the first liver passage is avoided, and that the dose of estrogen can be reduced.

These advantages make the gestagen-containing monotherapeutic agents of this invention appear to be especially suitable to treat, for example, endometriosis, gestagen-dependent tumors, benign breast diseases or the premenstrual syndrome.

The transdermal use of estrogens optionally in sequential or continuous combination with gestagen offers special advantages, for example, for treating menopausal symptoms, for the prevention of osteoporosis, for regulation of the menstrual cycle and for stabilization of the menstrual cycle.

The following embodiments are used for a more detailed explanation of the invention. The following commercial products were used in the embodiments:

Polyester film of 0.074 mm thickness (Skotchpak$^{(R)}$ 1009) of the 3M manufacturer; polypropylene film (Celgard$^{(R)}$ 2500) of the Celanese manufacturer, Linerfolie Skotchpak [liner film Scotchpak]$^{(R)}$ 1022 and 1360 of the 3M manufacturer; Transferkleber [transfer adhesive] 9871 of the 3M manufacturer, polyacrylester adhesive of Sichello$^{(R)}$ J 6610-21 type of the Henkel KG manufacturer, silicone adhesive of X-7-2960 type of the Dow Corning manufacturer and hydroxypropyl cellulose of the Klucel$^{(R)}$ HXF type of the Hercules manufacturer, polyisobutylene of Oppanol$^{(R)}$ B 15 SF type of the BASF AG company, dimethyl isosorbide of Arlasolve$^{(R)}$ DMI type of the ICI Surfactionts company, polyvinylpyrrolidone of Kollidon 12 PF type as well as the vinyl acetate-vinylpyrrolidone copolymers of Kollidon VA 64 type of the BASF AG company.

EXAMPLE 1

Figure 1:
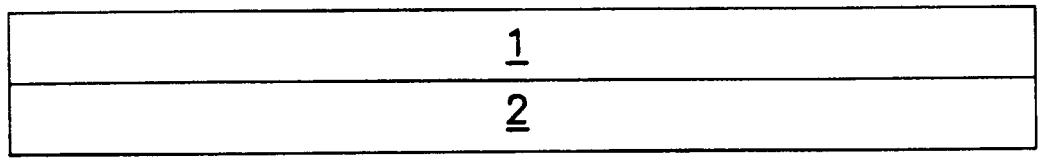
FIG. 1 shows a cross section through a simple round matrix system according to variant a without the removable protective layer. It consists of impermeable cover layer 1 and pharmaceutical agent-containing matrix layer 2.

0.8 g of desogestrel 8.0 g of dimethyl isosorbide are introduced in succession in 62.4 g of a 50% solution of silicone adhesive in benzine while being stirred. After the batch is degassed, the mixture is applied by a coating device to polyester film, so that after the volatile solvent is removed, a uniform film of 40 g/m$^2$ of solid coating results. Then, it is laminated with a fluoropolymer-coated polyester liner. The thus obtained laminate is divided by a punching device into round individual plasters of 10 cm$^2$ area and packaged in aluminum foil. FIG. 1 shows a cross section through this plaster without a polyester liner. After the liner film is removed, the plaster adheres to the skin.

The determination of content yields a uniform active ingredient distribution of 0.08 mg/cm$^2$ on average.

EXAMPLE 2

5.0 g of gestodene 10.0 g of dimethyl isosorbide are dissolved in succession in 170 g of a 50% solution of polyacrylester adhesive in acetone/benzine while being stirred. After the batch is degassed, the solution is applied by a coating device to polyester film, so that after the volatile solvent is removed, a uniform film of 100 g/m$^2$ of solid coating results. Then, it is laminated with a siliconized, active ingredient-free liner film. The thus obtained laminate is divided by a punching device into individual plasters of 10 cm$^2$ area and packaged in aluminum foil. After the liner film is removed, the plaster adheres to the skin.

The content of gestodene is 0.5 mg/cm$^2$ on average.

EXAMPLE 3

3.5 g of estradiol 3.5 g of levonorgestrel and 7.0 g of dimethyl isosorbide with 10% lauric acid are dissolved or suspended in succession in 112 g of a 50% solution of polyacrylester adhesive in acetone/benzine while being stirred. After the batch is degassed, the mixture is applied by a coating device to polyester film, so that after the volatile solvent is removed, a uniform film of 70 g/m$^2$ of solid coating results. Then, it is laminated with a siliconized, active ingredient-free liner film. The thus obtained laminate is divided by a punching device into individual plasters of 10 cm$^2$ area and packaged in aluminum foil. After the liner film is removed, the plaster adheres to the skin.

In a like manner, the content of estradiol and levonorgestrel is about 0.35 mg/cm$^2$ each.

EXAMPLE 4

Figure 2:
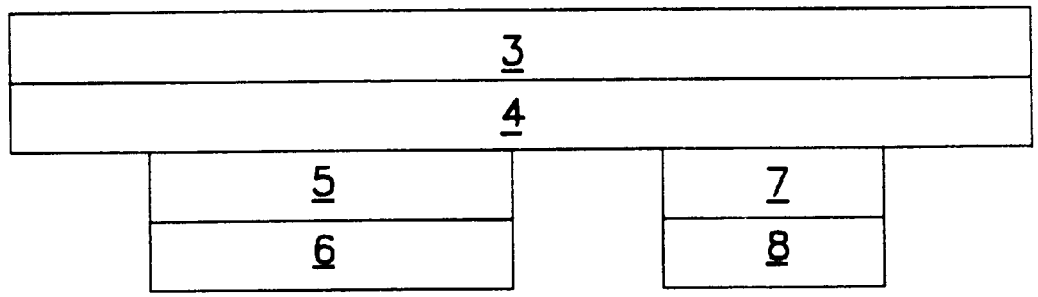
FIG. 2 shows a cross section through a matrix system according to variant b without the removable protective layer.
Figure 3:
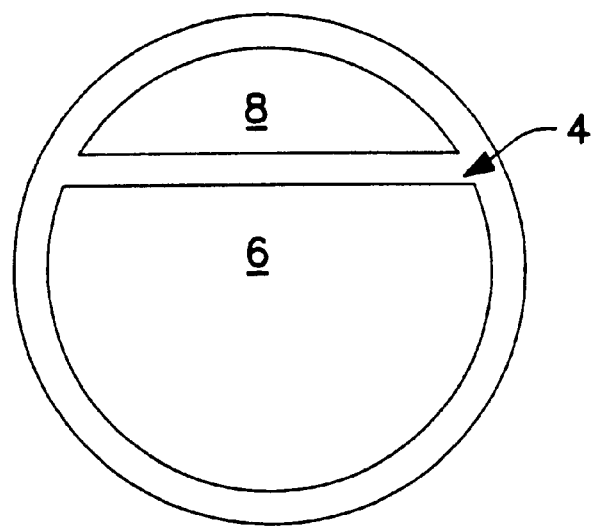
FIG. 3 shows a longitudinal section through this system. The system consists of cover 3, which is provided with a contact adhesive layer 4. Two pharmaceutical agent-containing matrix layers 6 and 8 are attached to this contact adhesive layer by impermeable covers 5 and 7.

Analogously to Example 1, two different segment-type matrix systems are produced, which have the design represented in FIGS. 2 and 3. Matrix system I consists of matrix layer 8—provided with a polyester film 7—of the following composition:

1.0 mg of norethisterone acetate 5.0 mg of dimethyl isosorbide and 44 mg of acrylate adhesive solid and has an area of 5 cm$^2$.

Matrix system II consists of matrix layer 6—provided with a polyester film 5—of the following composition:

2.0 mg of ethinylestradiol 10.0 mg of dimethyl isosorbide and 88 mg of acrylate adhesive solids and has an area of 10 cm$^2$.

Both matrix systems are bonded to a linen cloth that is coated with a skin contact adhesive, as FIG. 3 shows. After lamination and punching out, plasters of the type shown in FIGS. 2 and 3 result.

EXAMPLE 5

3.5 g of ethinylestradiol 3.5 g of desogestrel and 7.0 g of isopropyl myristate are added in succession to 112 mg of a 50% solution of polyisobutylene-plastic (Oppanol$^{(R)}$ B 15 SF of the BASF AG company) in acetone-benzine while being stirred, and prepared as described in Example 3.

EXAMPLE 6

1.0 g of gestodene 8.0 g of dimethyl isosorbide and 9.0 g of Kollidon 12 PF are dissolved in succession in 100 g of a 50% solution of polyacrylester adhesive in ethyl acetate/isopropanol while being stirred. After the batch is degassed, the mixture is applied by a coating device to polyester film, so that after the volatile solvent is removed, a uniform film of 80 g/m$^2$ of solid coating results. Then, it is laminated with a siliconized, active ingredient-free liner film. The thus obtained laminate is divided by a punching device into individual plasters of 15 cm$^2$ and packaged in aluminum foil. After the liner film is removed, the plaster adheres to the skin.

EXAMPLE 7

1.0 g of gestodene
2.0 g of estradiol
8.0 g of dimethyl isosorbide and
9.0 g of Kollidon 12 PF are dissolved in succession in 100 g of a 50% solution of polyacrylester adhesive in ethyl acetate/isopropanol while being stirred. After the batch is degassed, the mixture is applied by a coating device to polyester film, so that after the volatile solvent is removed, a uniform film of 80 g/m$^2$ of solid coating results. Then, it is laminated with a siliconized, active ingredient-free liner film. The thus obtained laminate is divided by a punching device into individual plasters of 15 cm$^2$ and packaged in aluminum foil. After the liner film is removed, the plaster adheres to the skin.

EXAMPLE 8

1.0 g of levonorgestrel
8.0 g of dimethyl isosorbide and
9.0 g of Kollidon 12 PF are dissolved in succession in 100 g of a 50% solution of polyacrylester adhesive in ethyl acetate/isopropanol while being stirred. After the batch is degassed, the mixture is applied by a coating device to polyester film, so that after the volatile solvent is removed, a uniform film of 80 g/m$^2$ of solid coating results. Then, it is laminated with a siliconized, active ingredient-free liner film. The thus obtained laminate is divided by a punching device into individual plasters of 20 cm$^2$ and packaged in aluminum foil. After the liner film is removed, the plaster adheres to the skin.

EXAMPLE 9

1.0 g of levonorgestrel
1.0 g of estradiol
8.0 g of dimethyl isosorbide and
9.0 g of Kollidon 12 PF are dissolved in succession in 100 g of a 50% solution of polyacrylester adhesive in ethyl acetate/isopropanol while being stirred. After the batch is degassed, the mixture is applied by a coating device to polyester film, so that after the volatile solvent is removed, a uniform film of 80 g/m$^2$ of solid coating results. Then, it is laminated with a siliconized, active ingredient-free liner film. The thus obtained laminate is divided by a punching device into individual plasters of 20 cm$^2$ and packaged in aluminum foil. After the liner film is removed, the plaster adheres to the skin.

EXAMPLE 10

2.0 g of estradiol
8.0 g of dimethyl isosorbide and
9.0 g of Kollidon VA 64 are dissolved in succession in 100 g of a 50% solution of polyacrylester adhesive in ethyl acetate/isopropanol while being stirred. After the batch is degassed, the mixture is applied by a coating device to polyester film, so that after the volatile solvent is removed, a uniform film of 80 g/m$^2$ of solid coating results. Then, it is laminated with a siliconized, active ingredient-free liner film. The thus obtained laminate is divided by a punching device into individual plasters of 15 cm$^2$ and packaged in aluminum foil. After the liner film is removed, the plaster adheres to the skin.

EXAMPLE 11

0.9 g of levonorgestrel
1.8 g of estradiol
19.0 g of dimethyl isosorbide
4.5 g of lauric acid and
13.5 g of Kollidon VA 64 are dissolved in succession in 170 g of a 38% solution of polyacrylester adhesive in ethyl acetate/isopropanol while being stirred. After the batch is degassed, the mixture is applied by a coating device to polyester film, so that after the volatile solvent is removed, a uniform film of 100 g/m$^2$ of solid coating results. Then, it is laminated with a siliconized, active ingredient-free liner film. The thus obtained laminate is divided by a punching device into individual plasters of 20 cm$^2$ and packaged in aluminum foil. After the liner film is removed, the plaster adheres to the skin.

EXAMPLE 12

0.9 g of levonorgestrel
19.0 g of dimethyl isosorbide
4.5 g of lauric acid and
13.5 g of Kollidon VA 64 are dissolved in succession in 170 g of a 38% solution of polyacrylester adhesive in ethyl acetate/isopropanol while being stirred. After the batch is degassed, the mixture is applied by a coating device to polyester film, so that after the volatile solvent is removed, a uniform film of 100 g/m$^2$ of solid coating results. Then, it is laminated with a siliconized, active ingredient-free liner film. The thus obtained laminate is divided by a punching device into individual plasters of 20 cm$^2$ and packaged in aluminum foil. After the liner film is removed, the plaster adheres to the skin.

EXAMPLE 13

0.9 g of gestodene
1.8 g of estradiol
19.0 g of dimethyl isosorbide
4.5 g of lauric acid and
13.5 g of Kollidon VA 64 are dissolved in succession in 170 g of a 38% solution of polyacrylester adhesive in ethyl acetate/isopropanol while being stirred. After the batch is degassed, the mixture is applied by a coating device to polyester film, so that after the volatile solvent is removed, a uniform film of 100 g/m$^2$ of solid coating results. Then, it is laminated with a siliconized, active ingredient-free liner film. The thus obtained laminate is divided by a punching device into individual plasters of 20 cm$^2$ and packaged in aluminum foil. After the liner film is removed, the plaster adheres to the skin.

EXAMPLE 14

0.9 g of gestodene
19.0 g of dimethyl isosorbide
4.5 g of lauric acid and
13.5 g of Kollidon VA 64 are dissolved in succession in 170 g of a 38% solution of polyacrylester adhesive in ethyl acetate/isopropanol while being stirred. After the batch is degassed, the mixture is applied by a coating device to polyester film, so that after the volatile solvent is removed, a uniform film of 100 g/m² of solid coating results. Then, it is laminated with a siliconized, active ingredient-free liner film. The thus obtained laminate is divided by a punching device into individual plasters of 20 cm² and packaged in aluminum foil. After the liner film is removed, the plaster adheres to the skin.

EXAMPLE 15

0.9 g of levonorgestrel 1.8 g of estradiol 19.0 g of dimethyl isosorbide 4.5 g of lauric acid and 13.5 g of Kollidon 12 PF are dissolved in succession in 170 g of a 38% solution of polyacrylester adhesive in ethyl acetate/isopropanol while being stirred. After the batch is degassed, the mixture is applied by a coating device to polyester film, so that after the volatile solvent is removed, a uniform film of 100 g/m² of solid coating results. Then, it is laminated with a siliconized, active ingredient-free liner film. The thus obtained laminate is divided by a punching device into individual plasters of 20 cm² and packaged in aluminum foil. After the liner film is removed, the plaster adheres to the skin.

EXAMPLE 16

0.9 g of levonorgestrel 19.0 g of dimethyl isosorbide 4.5 g of lauric acid and 13.5 g of Kollidon 12 PF are dissolved in succession in 170 g of a 38% solution of polyacrylester adhesive in ethyl acetate/isopropanol while being stirred. After the batch is degassed, the mixture is applied by a coating device to polyester film, so that after the volatile solvent is removed, a uniform film of 100 g/m² of solid coating results. Then, it is laminated with a siliconized, active ingredient-free liner film. The thus obtained laminate is divided by a punching device into individual plasters of 20 cm² and packaged in aluminum foil. After the liner film is removed, the plaster adheres to the skin.

EXAMPLE 17

0.9 g of gestodene 1.8 g of estradiol 19.0 g of dimethyl isosorbide 4.5 g of lauric acid and 13.5 g of Kollidon 12 PF are dissolved in succession in 170 g of a 38% solution of polyacrylester adhesive in ethyl acetate/isopropanol while being stirred. After the batch is degassed, the mixture is applied by a coating device to polyester film, so that after the volatile solvent is removed, a uniform film of 100 g/m² of solid coating results. Then, it is laminated with a siliconized, active ingredient-free liner film. The thus obtained laminate is divided by a punching device into individual plasters of 20 cm² and packaged in aluminum foil. After the liner film is removed, the plaster adheres to the skin.

EXAMPLE 18

0.9 g of gestodene 19.0 g of dimethyl isosorbide 4.5 g of lauric acid and 13.5 g of Kollidon 12 PF are dissolved in succession in 170 g of a 38% solution of polyacrylester adhesive in ethyl acetate/isopropanol while being stirred. After the batch is degassed, the mixture is applied by a coating device to polyester film, so that after the volatile solvent is removed, a uniform film of 100 g/m² of solid coating results. Then, it is laminated with a siliconized, active ingredient-free liner film. The thus obtained laminate is divided by a punching device into individual plasters of 20 cm² and packaged in aluminum foil. After the liner film is removed, the plaster adheres to the skin.

We claim:

1. A transdermal therapeutic system comprising
    at least one matrix layer having an active ingredient phase comprising one or more sex steroids and, in an amount of 1 to 40% by weight relative to the entire active ingredient phase, dimethyl isosorbide, and
    a skin contact adhesive,
    provided that 3-keto-desogestrel is not one of the sex steroids and provided that the system does not contain an active ingredient-containing, non-free-flowing gel phase.

2. The system of claim 1 wherein the one or more sex steroids include a gestagen, an estrogen or a combination thereof.

3. The system of claim 1 wherein the one or more sex steroids include gestodene, levonorgestrel, desogestrel, norethisterone or norethisterone acetate.

4. The system of claim 1 wherein the one or more sex steroids include estradiol, estriol, 17α-ethinylestradiol, mestranol, 14α,17α-ethanoestra-1,3,5(10)-triene-3,17β-diol, 14α,17α-ethanoestra-1,3,5(10)-triene-3,16α,17β-triol or an ester of one of these compounds.

5. The system of claim 1 wherein the one or more sex steroids include a gestagen and an estrogen.

6. The system of claim 1 wherein the one or more sex steroids include levonorgestrel.

7. The system of claim 1 wherein the one or more sex steroids include a gestagen and an estrogen in a concentration ratio of gestagen to estrogen of from 5:1 to 1:5.

8. The system of claim 1 additionally comprising a penetration enhancer.

9. The system of claim 1 additionally comprising a crystallization inhibitor.

10. The system of claim 1 wherein dimethyl isosorbide is provided in an amount of 5 to 25% by weight relative to the entire active ingredient phase.

11. The system of claim 1 which comprises:
    an impermeable cover layer;
    one to three matrix layer(s) containing the one or more sex steroids and dimethyl isosorbide adhered to the cover layer;
    a skin contact adhesive, optionally containing a penetration-enhancing agent, covering the matrix layer(s); and
    a removable protective layer over the skin contact adhesive.

12. The system of claim 1 which comprises:
    a cover having a contact adhesive and optionally a penetration-enhancing agent;
    one or two matrix layer(s) containing the one or more sex steroids and dimethyl isosorbide adhered to the cover layer such that they leave an adhesive border from the cover uncovered; and
    a removable protective layer.

13. The system of claim 11, which has only one matrix layer containing the one or more sex steroids.

14. The system of claim 11, which has two or three matrix layers each containing the one or more sex steroids.

15. The system of claim 11, which has a matrix layer containing a mixture of two or more different sex steroids.

16. The system of claim 12, which has only one matrix layer containing the one or more sex steroids.

17. The system of claim 12, which has two matrix layers each containing the one or more sex steroids.

18. The system of claim 12, which has a matrix layer containing a mixture of two or more different sex steroids.

19. A method for contraception, treatment of endometriosis, treatment of gestagen-dependent tumors or treatment of premenstrual syndrome which comprises administering a sex steroid transdermally by a system according to claim 1, wherein the one or more sex steroids do not include an estrogen.

20. A method for treatment of menopausal symptoms, prevention of osteoporosis, regulation or stabilization of the menstrual cycle or contraception which comprises administering a sex steroid transdermally by a system according to claim 1.

* * * * *